United States Patent [19]

Yamazaki et al.

[11] Patent Number: 5,218,868
[45] Date of Patent: Jun. 15, 1993

[54] SIGNAL PROCESSING METHOD FOR MAGNETIC-ULTRASONIC WALL THICKNESS MEASURING APPARATUS

[75] Inventors: Kazuo Yamazaki; Yoshioki Komiya, both of Tokyo; Mitsuo Sueyoshi; Takaaki Ogiwara, both of Osaka, all of Japan

[73] Assignee: NKK Corporation, Tokyo, Japan

[21] Appl. No.: 661,822

[22] Filed: Feb. 26, 1991

[30] Foreign Application Priority Data

Feb. 27, 1990 [JP] Japan .................................. 2-44581

[51] Int. Cl.⁵ ...................... G01N 29/10; G01N 29/22
[52] U.S. Cl. .................................................. 73/622
[58] Field of Search ................. 73/597, 609, 615, 616, 73/620, 622, 625

[56] References Cited

U.S. PATENT DOCUMENTS

| | | | |
|---|---|---|---|
| 4,099,418 | 7/1978 | Bennett et al. | 73/625 |
| 5,007,291 | 4/1991 | Walters et al. | 73/622 |
| 5,031,493 | 7/1991 | Dorr | 73/597 |

FOREIGN PATENT DOCUMENTS

| | | | |
|---|---|---|---|
| 57-203949 | 12/1982 | Japan . | |
| 57-203950 | 12/1982 | Japan . | |
| 59-18452 | 1/1984 | Japan . | |
| 1040242 | 8/1966 | United Kingdom | 73/622 |
| 2189602 | 10/1987 | United Kingdom | 73/620 |

Primary Examiner—Hezron E. Williams
Assistant Examiner—Rose M. Finley
Attorney, Agent, or Firm—Michael N. Meller

[57] ABSTRACT

In the on-line measurement of the wall thickness of a steel pipe, use is made of a rotary-type magnetic-ultrasonic wall thickness measuring apparatus capable of measuring the wall thickness of the steel pipe along the whole periphery circumferentially whereby measured data signals from the wall thickness measuring apparatus are reduced for each of a plurality of inspection blocks comprising small section established in a longitudinal direction of the steel pipe, and the resulting measured data groups are subjected to a pass-fail discrimination in according with predetermined criteria thereby making possible the control of such qualities as the wall thickness, thickness deviation rate and average inner diameter for each product.

11 Claims, 12 Drawing Sheets

SIGNAL PROCESSING METHOD FOR MAGNETIC-ULTRASONIC WALL THICKNESS MEASURING APPARATUS

BACKGROUND OF THE INVENTION

1. Field of the Invention

The present invention relates to a method of processing the measured thickness data signals produced in the course of the on-line measurement of the wall thickness of a pipe by the use of a rotary-type magnetic-ultrasonic wall thickness measuring apparatus.

2. Description of the Prior Art

Magnetic-ultrasonic wall thickness gages heretofore known in the art have been of the stationary type in which, as disclosed for example in Japanese Laid-Open Patent Nos. 57-203949, 57-203950 and 59-18452, a probe is fixedly placed in a given position relative to a material to be inspected and moreover it is so constructed that the magnetic flux produced from excitation coils arranged on the sides of the probe is passed in the longitudinal direction of the material to be inspected.

Figure 13:
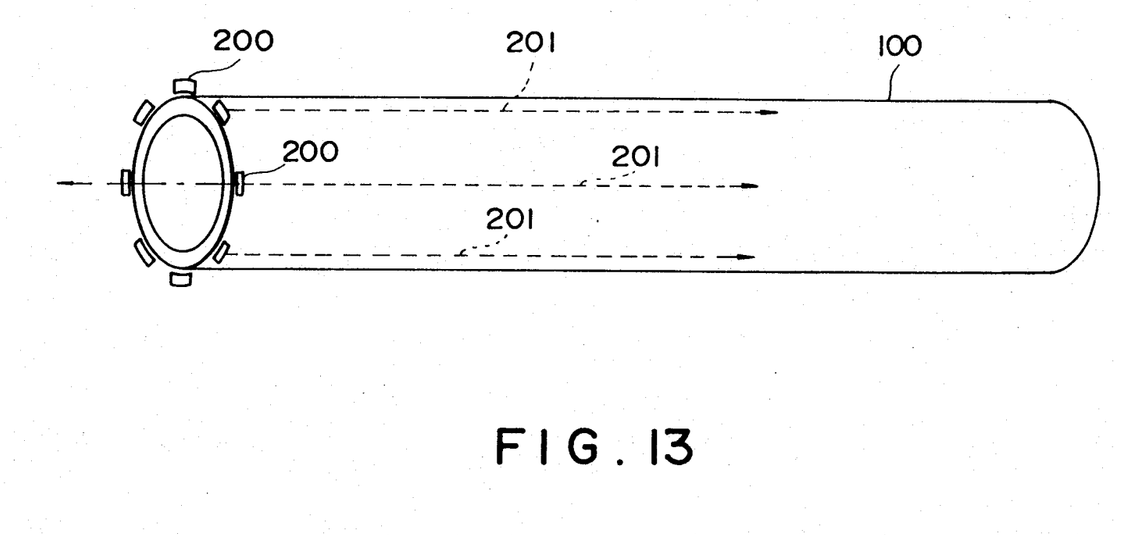
FIG. 13 is a schematic diagram showing a case where conventional stationary-type magnetic-ultrasonic wall thickness gages are used.

FIG. 13 of the accompanying drawings is a diagram for explaining a case in which the wall thickness of a steel pipe is measured by using conventional stationary magnetic-ultrasonic wall thickness gages. In Figure, numeral 100 designates a pipe to be inspected, and 200 stationary magnetic-ultrasonic wall-thickness gages which are arranged along the outer periphery of the pipe 100 at given intervals.

To measure the wall thickness, the pipe 100 is transferred at a given speed in the direction of an arrow a and in the excitation condition the probe (not shown) of each of the magnetic-ultrasonic wall thickness gages 200 transmits and receives a current pulse, thereby continuously measuring the wall thickness.

However, the conventional magnetic-ultrasonic wall thickness gage involves the following disadvantages.

(1) Since the magnetic flux passes in the longitudinal direction, there is the danger of magnetization in cases where the material to be inspected is a cold-worked steel pipe and the gage can be used only on hot-worked steel pipes. The reason is that in the case of a cold-worked steel pipe, there is the danger of the arc being caused to run out during the welding of the pipe ends thus giving risk to an inconvenience. Also, the provision of a demagnetizing operation is not suitable since it correspondingly complicates the process.

(2) Since the probe is complicated and large in construction and it can be used only in the stationary condition, the wall thickness cannot be measured along the whole periphery in the circumferential direction of a pipe. In the case of FIG. 13, each inspection track 201 is located on the longitudinal continuous straight line from the position at which the corresponding wall thickness gage 200 is arranged. As a result, it is impossible to measure the portion between the adjacent wall thickness gates 200, thus failing to provide a final quality assurance for the pipe.

(3) In order to measure the several circumferential locations of a pipe, several probes must be arranged in the circumferential direction of the pipe and the number of such probes is about 12 at the most. Also, in the case of a small-diameter pipe, it is impossible to arrange such a large number of probes. Thus, this is improper from the quality assurance point of view.

(4) Since the probes are constructed to be independent of one another, it is extremely expensive to arrange a large number of probes.

Figure 11:
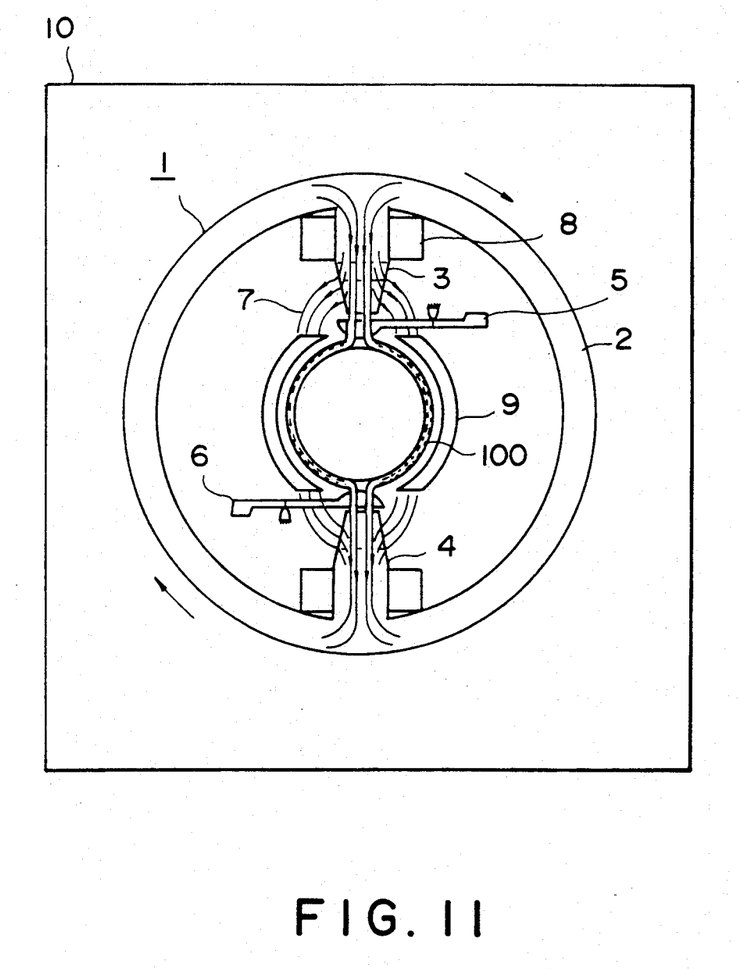
FIG. 11 is a sectional view showing the construction of the rotary-type magnetic-ultrasonic wall thickness measuring apparatus.

Then, as a means of overcoming these problems, there is known in the art a rotary-type magnetic-ultrasonic wall thickness measuring apparatus in which measuring heads are rotated about a pipe at a high speed. Its construction is shown in FIG. 11.

This rotary-type magnetic-ultrasonic wall thickness measuring apparatus 10 includes a rotary head 1 which is rotated at a high speed along the outer periphery of a pipe 100 to be inspected, and the rotary head 1 includes a ring yoke 2 having the common axis as the pipe 100, magnetic poles 3 and 4 which are arranged to project in a vertically opposite relationship on the inner side of the ring yoke 2 and two measuring heads 5 and 6 which are each supported on the rotary head 1 between the associated magnetic pole and the pipe 100 and having a plurality of longitudinal probes (not shown), thereby producing magnetic flux 7 passing in the circumferential direction of the pipe 100. In the Figure, numeral 8 designates magnetizing yokes, and 9 protective guides. The plurality of probes of each measuring head are arranged at given intervals in the longitudinal direction of the common magnetic pole.

While the operating principle of the rotary-type magnetic ultrasonic wall thickness measuring apparatus 10 is the same as the conventional gages, the pipe 100 is passed through the center of the rotary head 1 rotating at a speed of 1200 rpm at the maximum so that the resulting magnetic flux 7 is passed the circumferential direction of the pipe 100 thus eliminating the danger of magnetization and also the inspection tracks are in spiral form, thereby making it possible to measure the wall thickness of the pipe along its whole periphery in the circumferential direction irrespective of the pipe size.

The above-described rotary-type magnetic-ultrasonic wall thickness measuring apparatus has many advantages over the conventional gages of the stationary type and thus it is capable of performing an on-line inspection of the wall thickness of a steel pipe continuously along the whole periphery irrespective it being hot worked or cold worked and its pipe size.

Therefore, while the application of such rotary-type magnetic-ultrasonic wall thickness measuring apparatus to a continuous raw pipe in the pipe manufacturing process makes it possible to perform the desired high-speed and high-accuracy wall thickness measurement and discrimination, it is a general practice to supply products by cutting a single length of raw pipe into given lengths and therefore it is necessary to use a method for discriminating and processing large number of measured data groups individually for each of the products. In particular, where the wall thickness and inner diameter of the pipe ends are specified, a discriminating and processing method constitutes a particularly important problem and it is important from the standpoint of eliminating the off-line cutting and inspection, streamlining the inspection personnel and so on.

SUMMARY OF THE INVENTION

It is therefore an object of the present invention to provide a signal processing method for a rotary-type magnetic-ultrasonic wall thickness measuring apparatus whereby when making an on-line measurement and discrimination of the wall thickness of a steel pipe by use of the magnetic ultrasonic wall thickness measuring apparatus, it is made possible to effect the determination of measured data for every given short length of the pipe thereby ensuring the elimination of off-line cutting and inspection, the streamlining of inspection personnel, etc., as well as the improvement of the product quality assurance system.

It is another object of the present invention to provide a signal processing method for a magnetic-ultrasonic wall thickness measuring apparatus which is capable of effecting the discrimination and processing of data for every product and which is particularly well suited for controlling the wall thickness and inner diameter at the ends of a pipe.

To accomplish the above objects, in accordance with the present invention there is provided a signal processing method for a magnetic-ultrasonic wall thickness measuring apparatus featuring that in a wall thickness measuring method employing a rotary-type magnetic-ultrasonic wall thickness measuring apparatus in which magnetic heads each including probes are roatated along the outer periphery of a steel pipe which is transferred linearly so that the resulting magnetic flux is passed in the circumferential direction of the pipe and the transmission and reception of current pulses are effected under the excitation action thereby measuring the wall thickness of the pipe in accordance with the resulting ultrasonic waves, the steel pipe is divided in the longitudinal direction into a plurality of inspection blocks each having a given small length whereby wall thickness value data are gathered and reduced for the respective inspection blocks and the thus reduced wall thickness value data group of each inspection block is discriminated in accordance with given criteria thereby making a pass-fail discrimination on the inspection block.

By using the rotary-type magnetic-ultrasonic wall thickness measuring apparatus shown in FIG. 11, it is possible to obtain wall thickness value data on as many as, for example, 96 points per probe for every rotation of the wall thickness measuring apparatus and also it is possible together and reduce the data for each inspection block of a given small length in the longitudinal direction of the pipe, thereby obtaining the desired wall thickness value data group to be inspected. Therefore, by making a discrimination on each wall thickness value data group in accordance with the given standard, it is possible to make a pass-fail discrimination on the corresponding inspection block.

Such inspection blocks are established in the intermediary portion of a steel pipe excluding the crop portions at its ends. The reason is that the crop portions of the pipe are useless portions and their lengths are known by experiments thereby making it necessary to establish such inspection blocks only in the intermediary portion. Also, where the product length is specified, the positions of piece cutting points are also established so that particularly the wall thickness values at the pipe ends can be measured and also the thickness deviation rates and average inner diameters can be detected thus making it possible to control them as required by the user.

As the required pass-fail criteria for the inspection blocks, the items of the upper and lower limits of wall thickness control tolerance are selected and of wall thickness control tolerance are selected and established.

The reason for establishing the upper and lower limits of wall thickness control tolerance as the pass-fail criteria is an indication that this is necessary as far as the correction of the pipe ends at the post processing step is possible and its purpose is to contribute toward improving the yield.

Also, the outer diameter of the pipe is measured in addition to the above-mentioned wall thickness value data so as to calculate and discriminate the average inner diameter of the inspection blocks in accordance with the outer diameter data and the wall thickness value data.

Further, the wall thickness value data of the inspection blocks are developed in both the longitudinal and circumferential directions of the pipe and are indicated or recorded. By so doing, it is possible to utilize the data for crop length designing purposes as well as shape discriminating purposes.

As a result of the foregoing, irrespective of the size of a steel pipe and irrespective of the pipe being cold worked or hot worked, not only the on-line measurement of the wall thickness of the steel pipe is made possible along the whole periphery circumferentially but also the pass-fail discrimination of the pipe is made possible with respect to the respective short-length inspection blocks, thereby eliminating the need for off-line cutting and inspection and making it possible to reduce the off flow rate by 5% or more.

As the result of the foregoing, it is also possible to reduce the inspection personal by more than 9 persons than previously and the streamlining is made possible.

Still further, the wall thickness, thickness deviation rate and average inner diameter of a steel pipe can be measured at the pipe ends and along the whole pipe length in real time, thereby ensuring the precise quality assurance for products.

DESCRIPTION OF THE PREFERRED EMBODIMENTS

Figure 1:
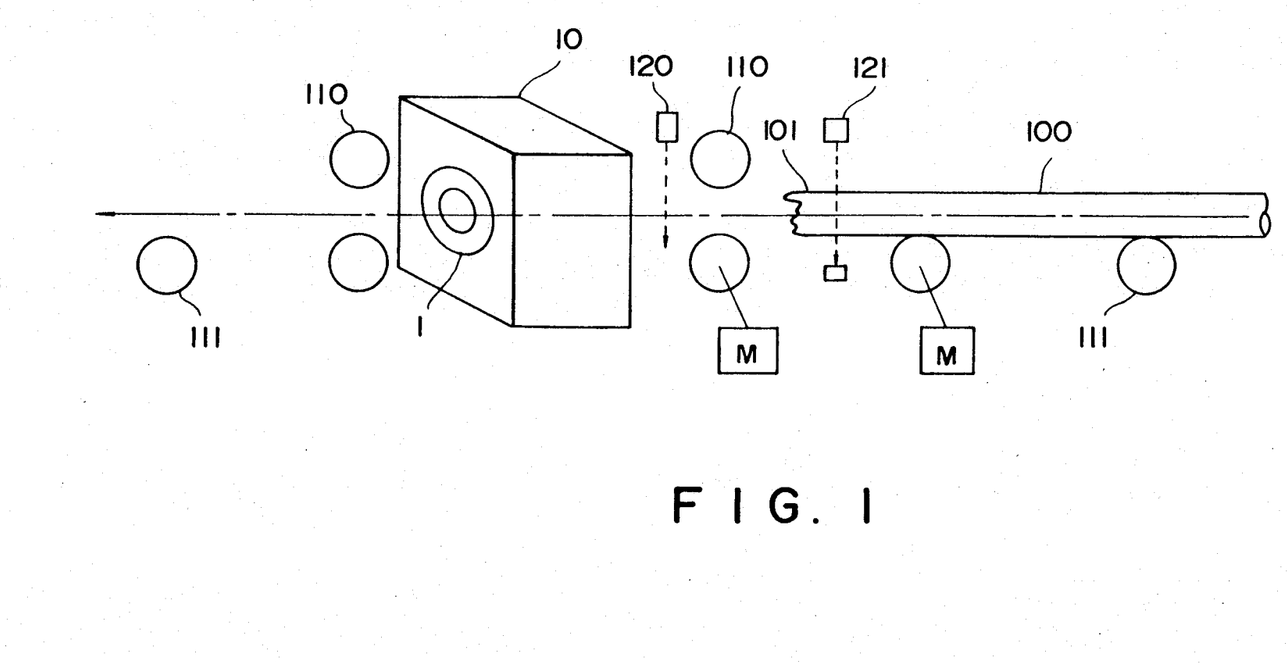
FIG. 1 is a schematic diagram of a wall thickness measuring apparatus used with the present invention.

Referring to FIG. 1, there is illustrated a schematic general view of a wall thickness measuring apparatus adapted for the on-line measurement of the wall thickness of a steel pipe. A pipe 100 to be inspected is linearly transferred by pinch rollers 110, transfer rollers 111, etc., at a given speed and its wall thickness is continuously measured along its whole periphery by a rotary-type magnetic-ultrasonic wall thickness measuring apparatus 10 arranged on the line. The principal internal construction of the wall thickness measuring apparatus 10 is as shown in FIG. 11.

Arranged in the rear of the wall thickness measuring apparatus 10 is a laser linear scale 120 which measures the length from the forward end of a crop portion 101 of the pipe 100. Also, the outer diameter of the pipe 100 is measured by an outer diameter gage 121 comprising a light sensor.

Figure 2:
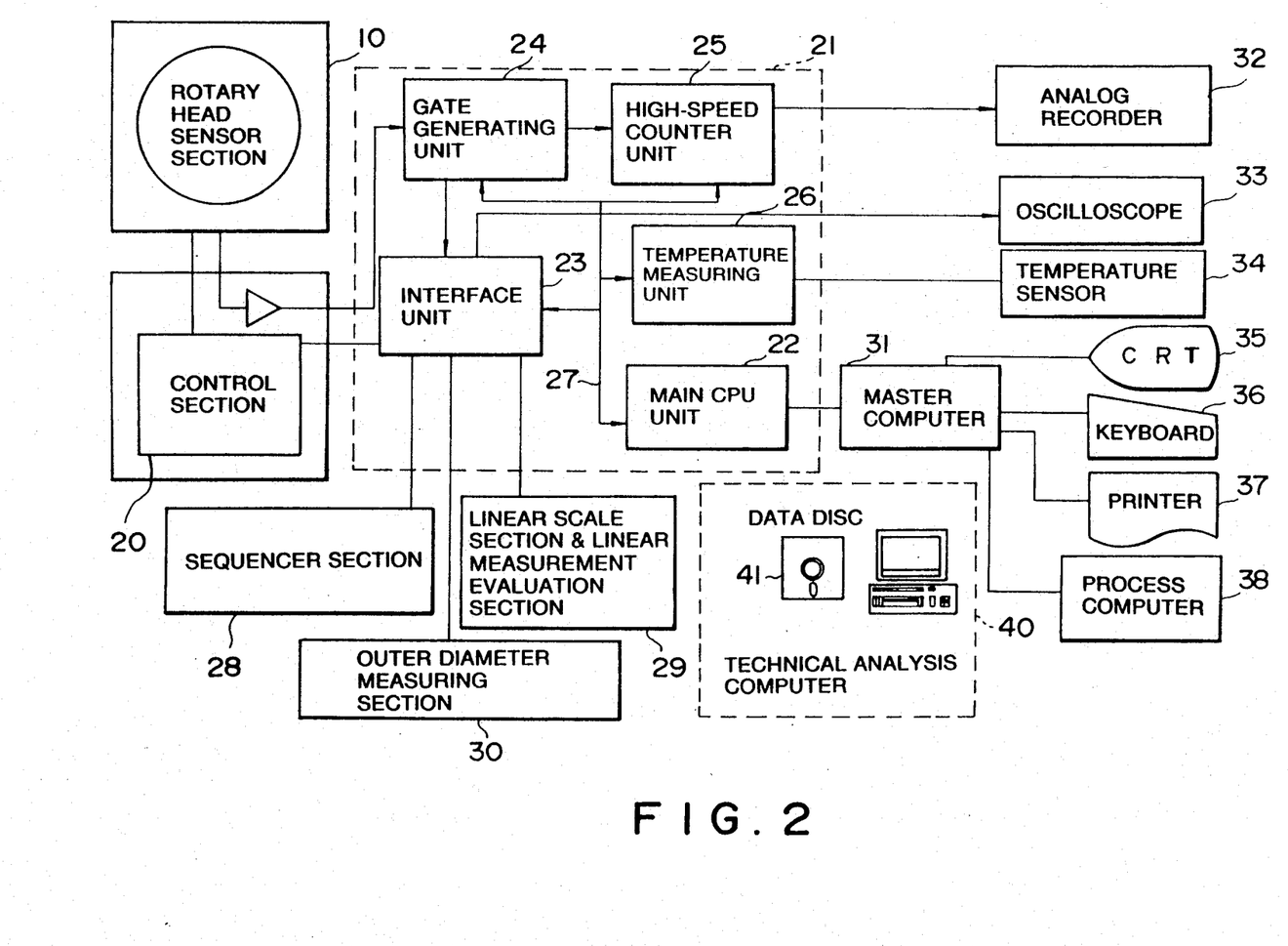
FIG. 2 is a control block diagram applied to a signal processing method according to the present invention.

The controller of the wall thickness measuring apparatus is constructed as shown in FIG. 2. In the Figure, numeral 20 designates a control section for controlling the rotational speed of a rotary head 1 of the rotary-type magnetic-ultrasonic wall thickness measuring apparatus 10 and the pulse current, voltage or the like to be applied to measuring heads 5 and 6 and the controls are effected through a main CPU unit 22 and an interface unit 23 of a data evaluation section 21. The data evaluation section 21 includes the main CPU unit 22, the interface unit 23 a gate generating unit 24, a high-speed counter unit 25 and a temperature measuring unit 26 and these units are connected with one another by a bus 27.

The gate generating unit 24 generates gates each used to measure the time interval between the transmitting wave generated from each of the probes of the measuring heads and a first echo and the gates are counted by the high-speed counter unit 25 to measure the wall thickness of the pipe.

The temperature measuring unit 26 has the purpose of providing compensation for variations in the sound velocity due to the temperature of the pipe to be inspected.

On the other hand, a sequencer section 28, a linear scale section and linear measurement evaluation section 29 and an outer diameter measuring section 30 are connected to the interface section 23. The sequencer section 28 controls the transfer mechanism, including the pinch rollers 110, the transfer rollers 111, etc., and the linear scale section and linear measurement evaluation section 29 counts the pulse signals of 0.1 mm generated from the laser linear scale 120 to thereby measure the lengths of the crop portions, the inspection blocks, etc., shown in FIG. 3. The outer diameter measuring section 30 receives the outer diameter data from the outer diameter gage 121 of FIG. 1.

These units and equipment are controlled by the main CPU unit 22 and condition setting, etc., are effected through a master computer 31. In FIG. 2, numeral 32 designates an analog recorder, 33 an oscilloscope, 34 a temperature sensor, 35 a CRT, 36 a keyboard, 37 a printer, and 38 a process computer comprising a higher-rank computer. Also, the data from the evaluation section 21 can be stored on a floppy disk 41 so that it is analyzed by a technical analytic computer 40.

Figure 3:
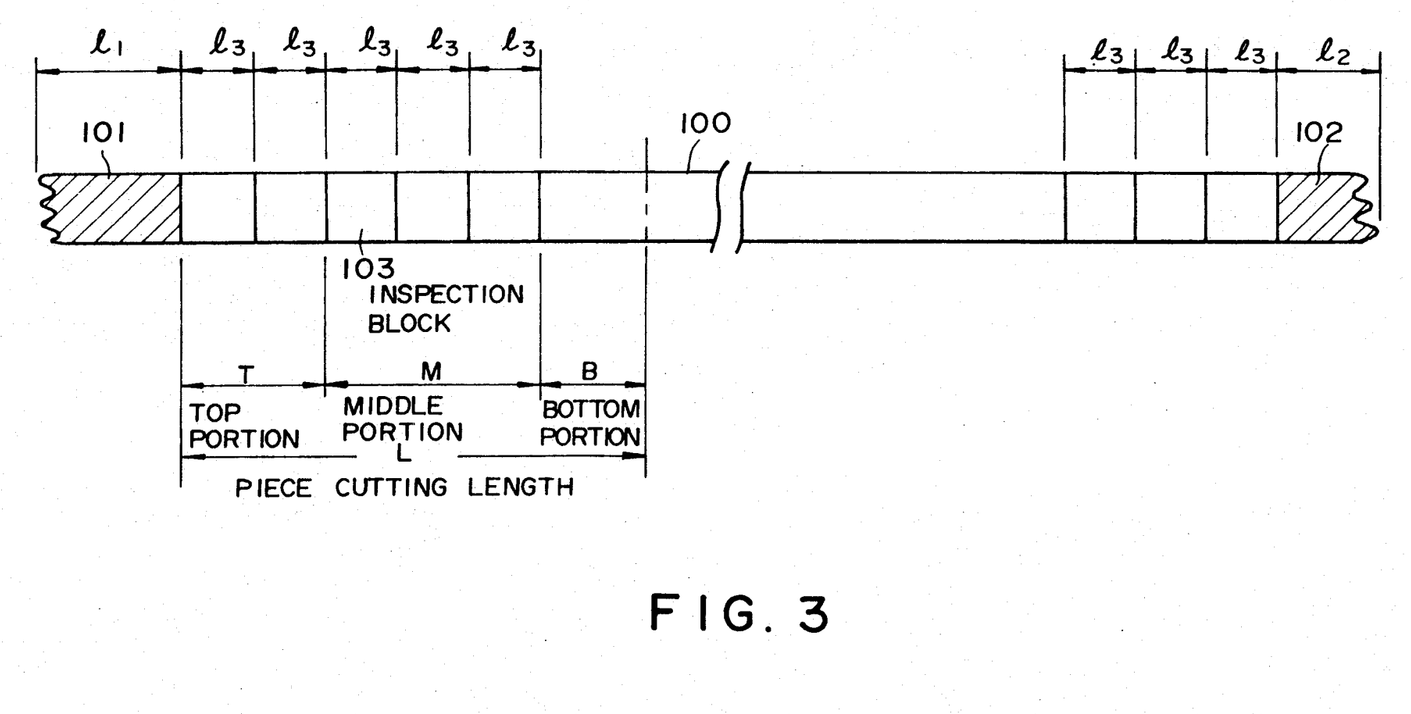
FIG. 3 is a diagram for explaining the method of establishing inspection blocks for obtaining wall thickness value data of a pipe to be inspected.

Also, FIG. 3 shows a wall thickness value data gathering method for the pipe 100 to be inspected.

Firstly, the crop portions 101 and 102 at the forward and rear ends of the pipe are waste portions and no data are gathered from these portions. Then, lengths $l_1$ and $l_2$ of these crop portions are separately inputted and set by the system master of FIG. 2 and are measured by the laser linear scale 120. It is to be noted that the crop portions are portions which will be cut off by a post-operation.

Then, established in the intermediary portion of the pipe are short inspection blocks 103 which are divided at regular intervals of $l_3 = 100$ mm, for example. Also, where a plurality of products are produced from the single raw continuous pipe, a piece cutting length L corresponding to the standard length of products, e.g., L = 5,500 mm is additionally established. The piece cutting length L is further divided into a top portion T, a middle portion M and a bottom portion B. The lengths of the top portion T, the bottom portion B and the crop portions 101 and 102 are set in centimeters.

Figure 4A:
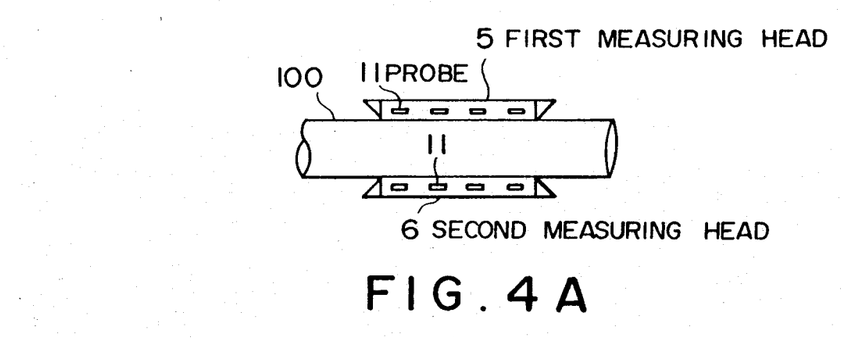
FIG. 4(a) is a schematic diagram showing the measuring heads of the rotary-type magnetic-ultrasonic wall thickness measuring apparatus used with the present invention.

In the magnetic-ultrasonic wall thickness measuring apparatus 10 of FIG. 1, the rotary head 1 is rotated at a high speed (1200 rpm at the maximum) during the wall thickness measurement. As shown in FIG. 4(a), the two measuring heads 5 and 6 arranged on the rotary head 1 are each provided with 4 (8 in total) probes 11 which are arranged at intervals for example of 20 mm in the longitudinal direction of the pipe 100 to be inspected so that each probe acquires the wall thickness value data of 96 points per rotation and these measured data are gathered and reduced for every inspection block lengths of 100 mm.

Figure 4B:
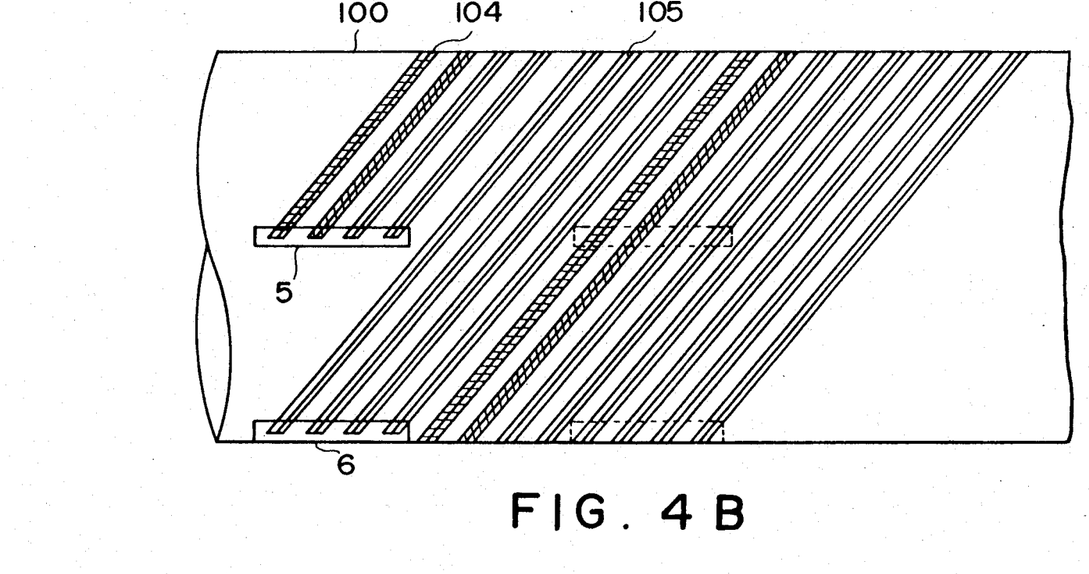
FIG. 4(b) is a schematic diagram showing the paths of the probes of the measuring heads on the pipe.

The inspection tracks 104 shown in FIG. 4(b) are the paths of the probes 11 of the first measuring head 5 and the other inspection tracks 105 are the paths of the probes 11 of the second measuring head 6. All of the inspection tracks take a helical form due to the rotation of the measuring heads. As a result, the wall thickness of the pipe can be measured along the whole periphery in the longitudinal direction. Then, wall thickness value data are gathered and reduced (the resulting set of the gathered and reduced wall thickness value data are referred to as "measured data groups") for the respective inspection blocks 103 as the result of the helical scanning by the probes and a pass-fail discrimination processing of the corresponding inspection blocks is performed on the thus gathered measured data groups in accordance with the procedure shown in FIG. 5.

Figure 5:
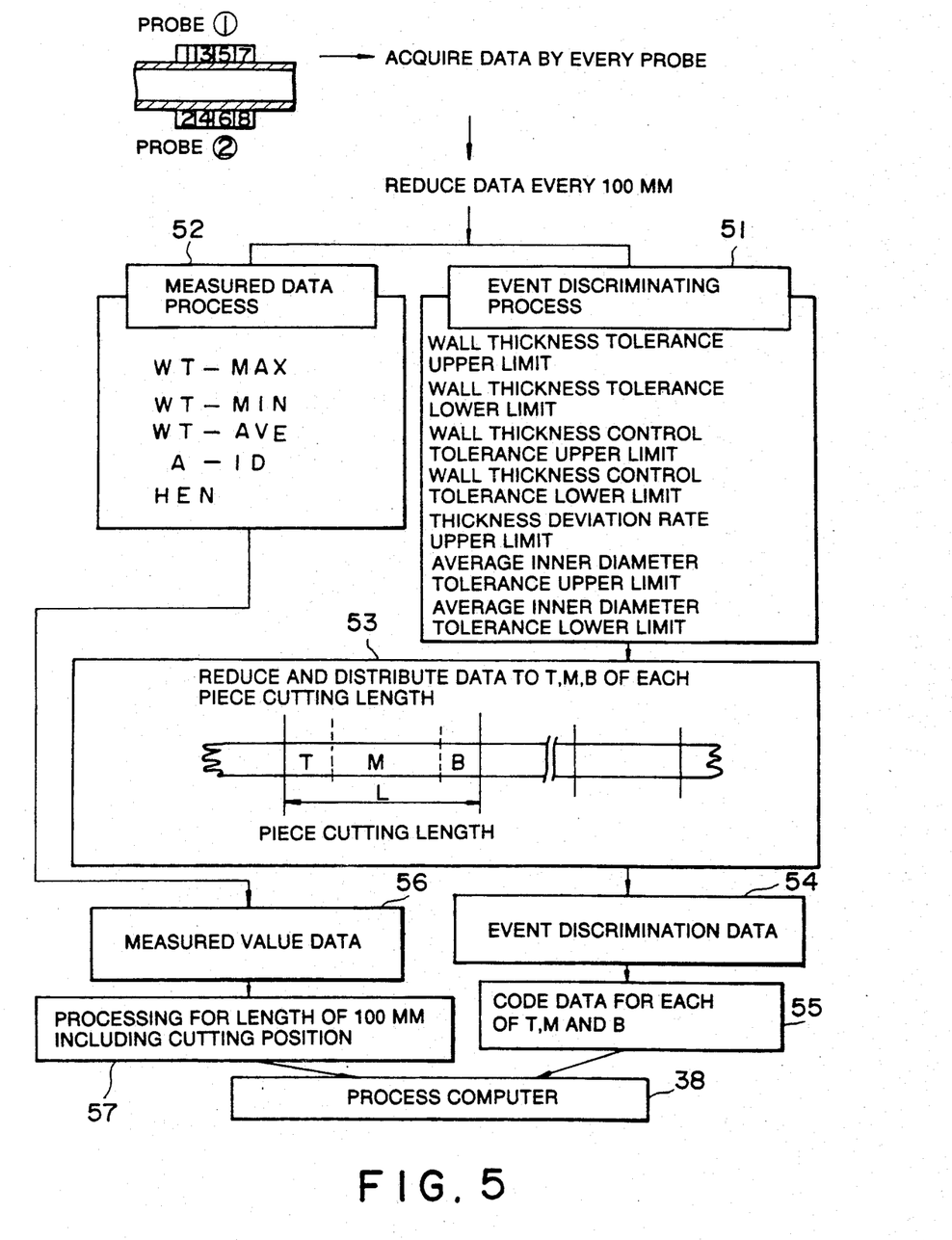
FIG. 5 is a flow chart showing the outline of a processing method for the measured data groups gathered and reduced for the respective inspection blocks.

As shown in FIG. 5, wall thickness value data are acquired from the respective probes of the first and second measuring heads (channels No. 1 to 8) and the data are gathered and reduced for every 100 mm of the pipe, thereby performing first an event discrimination process 51 is performed as the pass-fail criteria for the inspection blocks. The event discrimination process 51 gathers and reduces the data so as to be respectively distributed to the T, M and B portions of each piece cutting length (step 53). Here, the pass-fail data items used are as follows.

(1) Wall thickness tolerance upper limit (mm)
(2) Wall thickness tolerance lower limit (mm)

These items are set in accordance with the specifications of the user.

(3) Wall thickness control tolerance upper limit (mm)
(4) Wall thickness control tolerance lower limit (mm)

The wall thickness control tolerance is selected to be such that adjustments such as fitting can be effected by a post-operation and it is a set value obtained by adding to or subtracting a given value from the wall thickness tolerance. It is solely a control target value on the side of the maker.

(5) Thickness deviation rate upper limit (%)

The control target value in cases when the wall thickness value at the pipe ends is specified.

(6) Average inner diameter tolerance upper limit (mm).
(7) Average inner diameter tolerance lower limit (mm).

These are also used in cases where the inner diameter at the pipe ends is specified.

Then, at a measured data processing step 52, the processing is performed on the following items.

(1) Maximum wall thickness (WT-MAX) (mm)
The maximum wall thickness value for each length of 100 mm.

(2) Minimum wall thickness (WT-MIN) (mm)
The minimum wall thickness value for each length of 100 mm.

(3) Average wall thickness value (WT-AVE) (mm)
This is given by the following expression.

$$WT - AVE = \frac{\sum_{k=1}^{n} WT(k)}{n} \qquad 1$$

where
n = number of measuring points (within 100 mm)
WT = wall thickness value (4) Thickness deviation rate (HEN) (%)
Expression:

$$HEN = \frac{(WT - MAX) - (WT - MIN)}{NOR} *100 \qquad 2$$

where NOR = set wall thickness value (5) Average inner diameter (A-ID) (mm)
Expression:

$$A\text{-}ID = OD\text{-}(WT\text{-}AVE *2) \qquad 3$$

where OD = outer diameter (measured value from outer diameter gage)

It is to be noted that the pipe end lengths (the lengths of the portions T and B) of the respective pieces are set to 3 levels (500, 1000 and 1500 mm) in the system master.

At a processing step 55, event discrimination data 54 is respectively coded for the portions T, M and B and transferred to the process computer 38.

Also, at a step 57, measured value data 56 is processed for each length of 100 mm including the piece cutting position and similarly transferred to the process computer 38.

Figure 6:
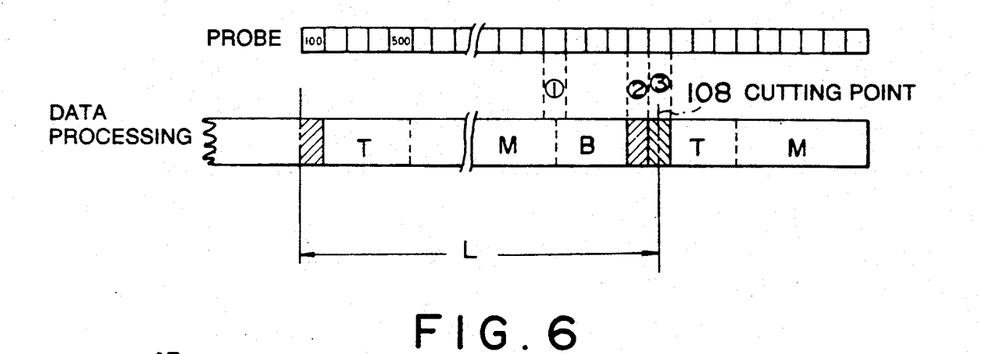
FIG. 6 is a diagram for explaining the processing method for each pipe length of 100 mm including a piece cutting position.

Here, the processing of each length of 100 mm including the piece cutting position denotes data processing in cases where the cutting points 108 of the pieces cannot be marked off at intervals of 100 mm and only the data of 100 mm before the cutting point is processed as shown in FIG. 6. As a result, the data of ①  means the processing of the portion B and only the data of 100 mm before the cutting point or ②  is processed when the cutting point represents a change of data for the measured value data. Also, the data of ③  denotes the processing of the leading 100 mm of the next portion T.

Figure 7A:
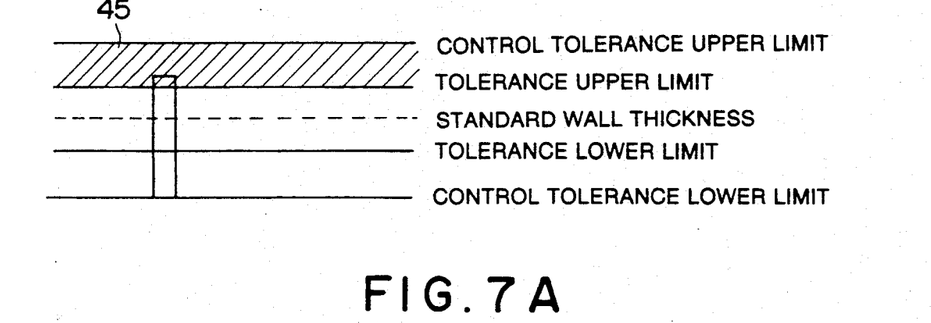
FIG. 7(a) is a diagram for explaining a pass-fail discrimination method for the measured data obtained by ¼ of a rotation.

Referring now to FIG. 7(a), there is illustrated a quarter (¼)-turn, method as an example of a pass-fail discrimination method of measured data. In other words, the pass-fail discrimination is possible if the measured data is not less than the tolerance upper limit and not greater than the control tolerance upper limit and also the measured data is within one fourth of a revolution. In the Figure, a hatched area 45 is a pass-fail selection enable range of measured data. The control tolerance is established particularly for such purposes that the pipe end is ground when its wall thickness is slightly greater than the tolerance or the pipe end is cut off when the length measurement is allowable.

Figure 7B:
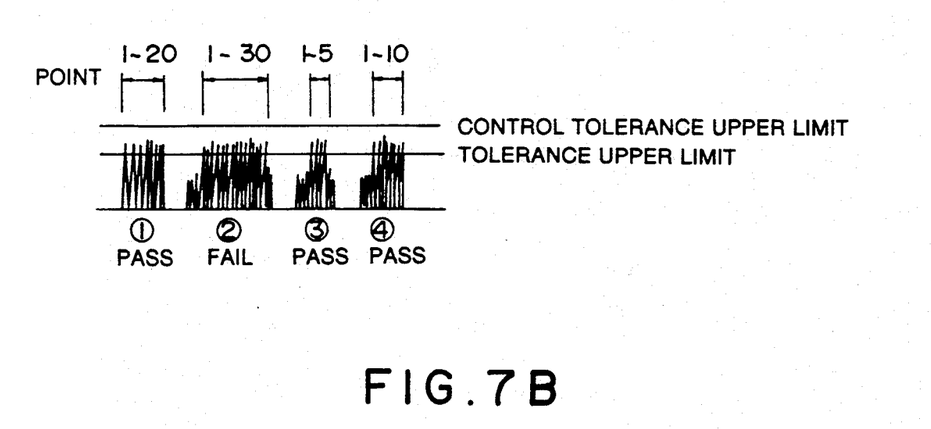
FIG. 7(b) is a diagram showing examples of the pass and fail of measured data according to the discrimination method of FIG. 7(a).

Then, the quarter-turn processing is a method of performing the processing on one fourth of the measured data of each probe (which measures 96 points). In other words, the continuous discrimination is performed on 96 points/4 = 24 points. For instance, as shown in FIG. 7(b), when the tolerance upper limit is shown in excess of the consecutive 24 points as the result of the quarter-turn processing (in the case of the measured data b), a fail indicative event is generated. On the contrary, when the tolerance upper limit indicative data is less than the consective 24 points (in the case of the measured data of a, c and d), a pass discrimination is made. The processing of the consecutive 24 points is started in response to the measurement of a level which is not less than the tolerance upper limit and not greater than the control tolerance upper limit. When the level decreases in the course of the processing, it is determined passable and the processing is not effected until the level of the next quarter-turn.

Therefore, the conditions of the pass-fail criteria are given as follows:

wall thickness tolerance upper limit < continuous

96/4 < wall thickness control tolerance upper limit.

The above-mentioned quarter-turn pass-fail discrimination method is mainly applied to a raw continuous pipe which is subjected to secondary operations such as cold drawing before shipping.

Figure 8:
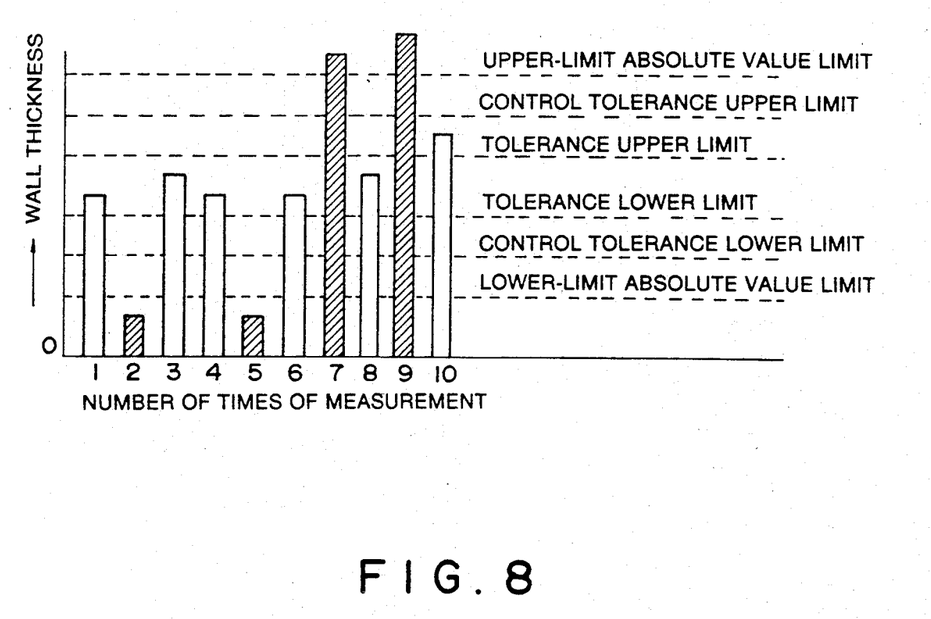
FIG. 8 is a diagram showing a method of discriminating abnormal data.

Referring now to FIG. 8, there is illustrated a discrimination method used in cases where abnormal data is produced in the measured data. This method effects the discrimination of data by setting the absolute value limits to the upper limit and the lower limit. In other words, a certain value x.xx mm is added to the tolerance upper limit so that any value greater than the resulting value is regarded as abnormal data. Also, the certain value x.xx mm is subtracted from the tolerance lower limit so that any value smaller than the resulting value is regarded as abnormal data. In this way, as for example, the second, fifth, seventh and ninth measured data indicated by the hatching in the Figure become abnormal data. The abnormal data are considered as if they were not measured.

The method of discriminating between valid and invalid data is performed in accordance with the following expressions:

abnormal data when $\Delta t_1 + \Delta t_2 > x.xx$ mm valid data when $\Delta t_1 + \Delta t_2 \leq x.xx$ mm where $\Delta t_1$ = absolute value of (current value-preceding value)

$\Delta t_2$ = absolute value of (current value-next value)

Figure 9:
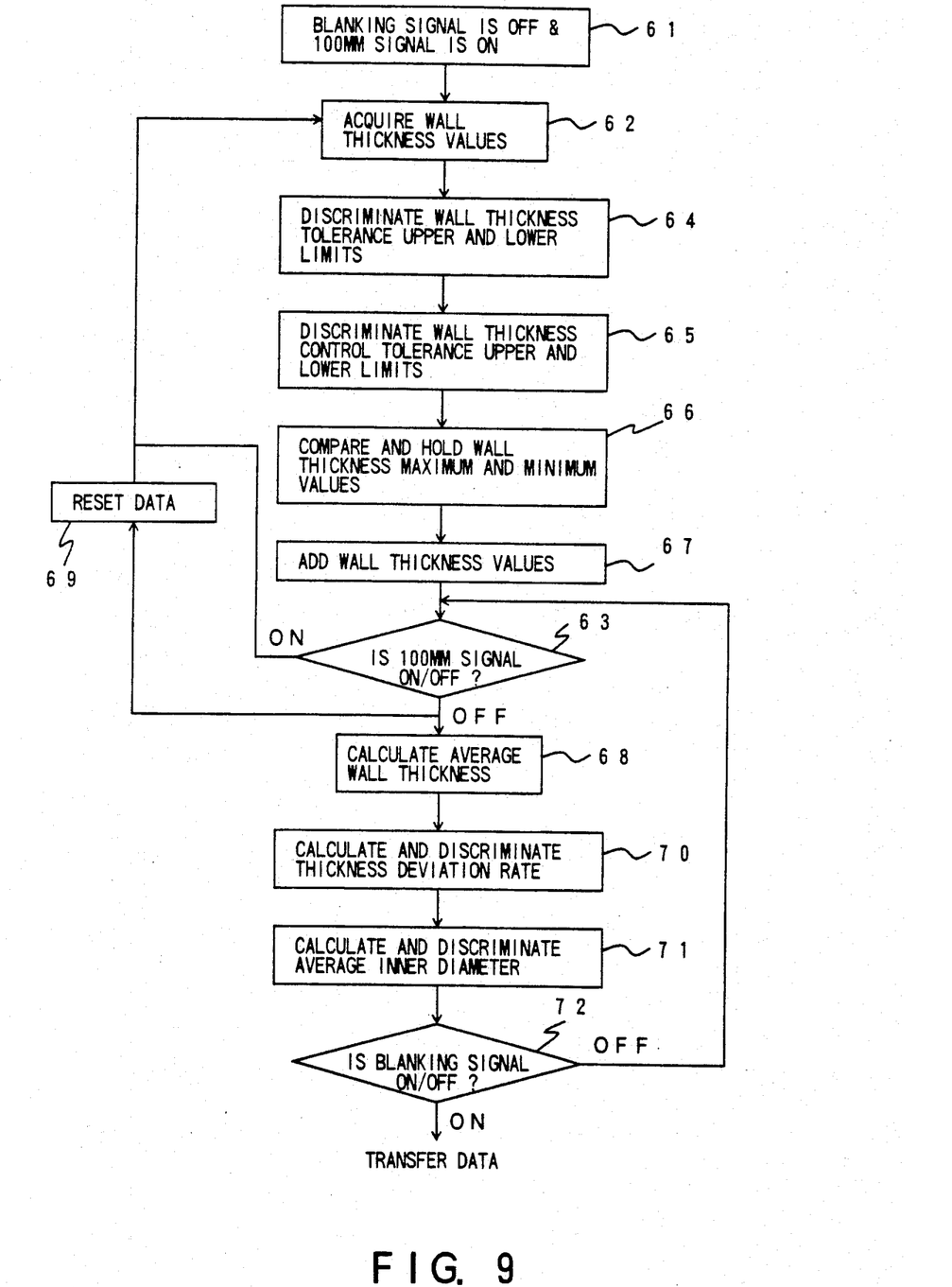
FIG. 9 is a flow chart showing the ordinary operation of the data evaluation section in FIG. 2.

FIG. 9 is a flow chart showing the operation of the evaluation section in FIG. 2 or the signal processing method during the ordinary wall thickness measurement.

Firstly, at a step 61, a blanking signal designating the intermediary portion of the pipe 100 excluding the crop portions 101 and 102 is turned off and simultaneously a 100 mm signal designating the inspection block length $l_3 = 100$ mm is turned on, thereby starting the wall thickness measurement.

The wall thickness value data on 96 points per revolution for every probe is acquired at a step 62, and at a step 63, the data is repeatedly reduced every 100 mm until the 100 mm signal is turned off. In other words, the measured data of the inspection block subject to pass-fail discrimination is produced.

Then, with respect to the measured data of the event decisions items shown in FIG. 5, the wall thickness upper and lower limits are discriminated first (step 64) and then the wall thickness control tolerance upper and lower limits are discriminated (step 65). Then, the wall thickness maximum and minimum values within the length of 100 mm are compared and the respective maximum and minimum values are held (step 66). Then, the wall thickness values are added (step 67) and an average wall thickness value is calculated according to equation 1. When the 100 mm signal is turned off, the data reduced up to that time is reset (step 69).

After the average wall thickness value has been calculated at the step 68, the calculation and discrimination of a thickness deviation rate are effected according to equation 2 (step 70). Then, the calculation and discrimination of an average inner diameter are effected in accordance with equation 3 (step 71). These calculations are repeated until the blanking signal is turned on.

Figure 10:
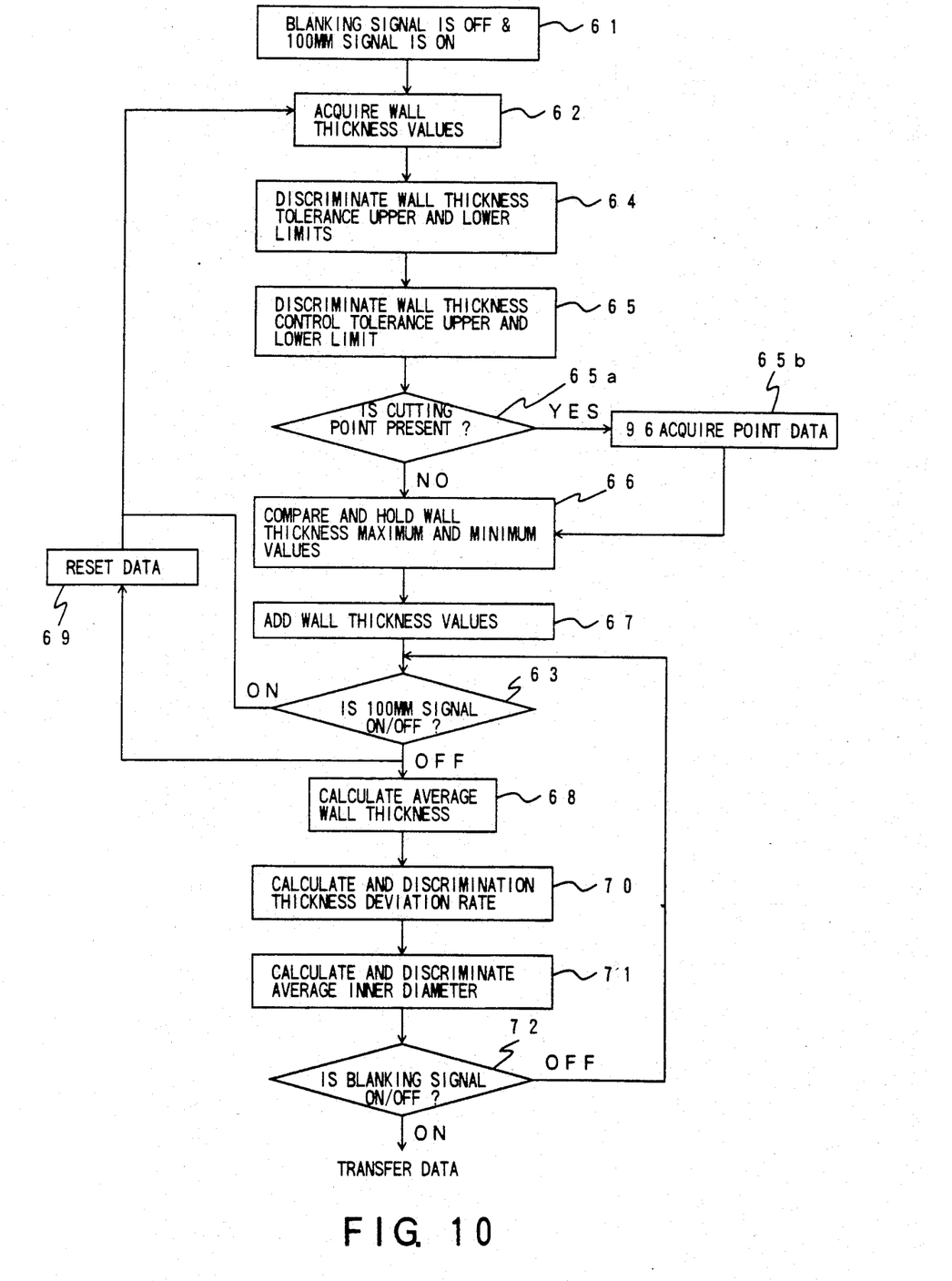
FIG. 10 is a flow chart showing the operation of the data evaluation section when used for the purpose of technical analysis.

Referring now to FIG. 10, there is illustrated a flow chart showing a signal processing method adapted to be used for technical analysis purposes such as the designing of crop lengths and the shape discrimination. In this case, a process step 65a for determining the presence or absence of a cutting point is included between the previously mentioned steps 65 and 66 and data of 96 points at the cutting point is acquired (step 65). The rest is the same as in the case of FIG. 9.

Figure 12A:
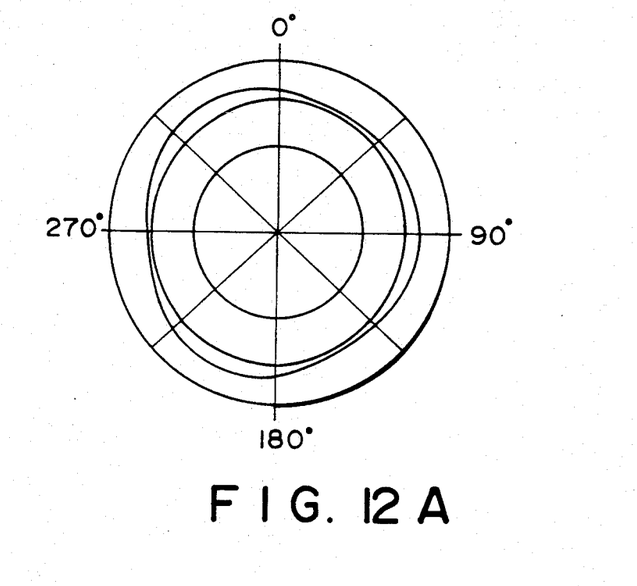
FIGS. 12(a) and 12(b) showing respectively examples of wall thickness value data developed in the circumferential and longitudinal direction of the pipe.
Figure 12B:
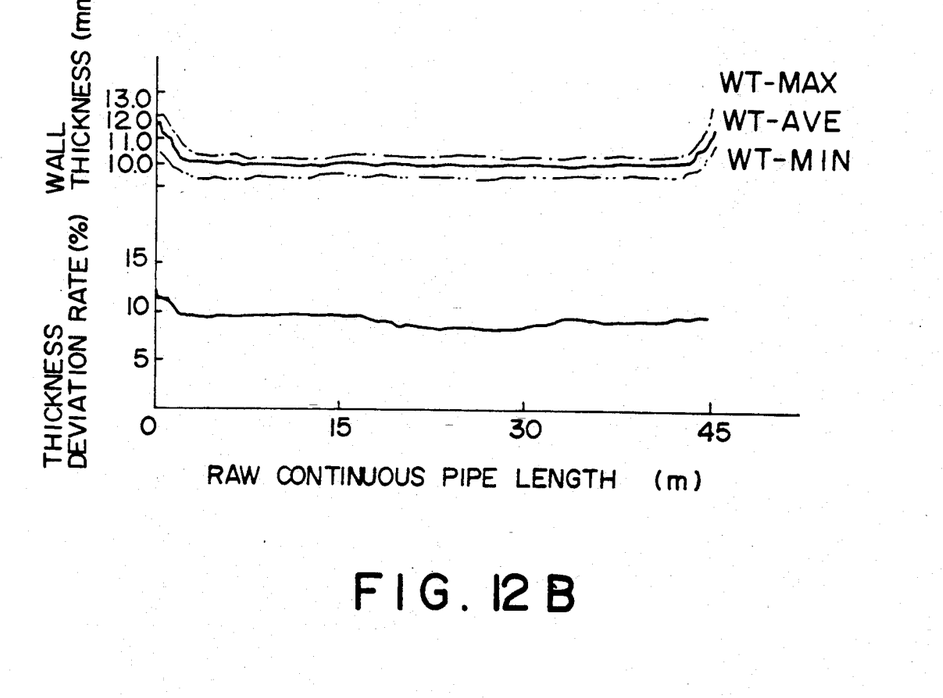

FIGS. 12(a) and 12(b) respectively show examples of developments of the thus obtained data in the circumferential and longitudinal directions of the pipe. It is possible to make the necessary modification, improvement, etc., on the rolling process for steel pipes in accordance with the judgements made from the indication of these developments.

Also, as regards the indication of rejected wall thickness values, commands are applied to a marking unit (not shown) installed on the steel pipe transfer line thereby making marks on the corresponding portions.

We claim:

1. A method for measuring the thickness of steel pipe comprising the steps of:

employing a rotary-type magnetic-ultrasonic wall thickness measuring apparatus wherein a plurality of measuring heads each having a plurality of probes are rotated along an outer periphery of said steel pipe transferred linearly whereby magnetic flux is passed in a circumferential direction of said steel pipe, and the transmission and reception of current pulses are effected under the action of excitation thus producing ultrasonic waves;

measuring a wall thickness of said steel pipe using a signal processing apparatus with said magnetic-ultrasonic wall thickness measuring apparatus further comprising the signal processing steps of:

measuring a length from a pipe end to the transferring steel pipe continuously and dividing the measured value of length to create a plurality of inspection blocks, said plurality of inspection blocks each including a section of a predetermined small length in a longitudinal direction of said steel pipe;

gathering and reducing wall thickness value data for each of said plurality of inspection blocks; and deriving from said rotary-type magnetic ultrasonic wall thickness measuring apparatus discrimination data from said reduced wall thickness value data group in accordance with predetermined criteria to make a pass-fail discrimination of each said inspection block and recording the wall thickness of steel pipe continuously along an outer periphery thereof on the basis of result of said discrimination step.

2. A signal processing method in said step of measuring said pipe and dividing said pipe into said plurality of inspection blocks as in claim 1, wherein said inspection blocks are established in an intermediary portion of said steel pipe excluding a length of crop portions thereof.

3. A signal processing method in said step of pass-fail discrimination of inspection block as in claim 1, wherein said inspection block pass-fail criteria comprises values of wall thickness tolerance upper and lower limits as well as wall thickness control tolerance upper and lower limits.

4. A signal processing method as in claim 1, wherein positions of piece cutting points corresponding to standard lengths of products are determined in addition to create said inspection blocks.

5. A signal processing method as in claim 1, wherein an average inner diameter in each of said plurality of inspection blocks is calculated in accordance with measured outer diameter data of said steel pipe and the wall thickness value data of each said inspection block and thereby the inner diameter is controlled by the average inner diameter.

6. A signal processing method as in claim 1, wherein the wall thickness value data of each of said plurality of inspection blocks is developed in the longitudinal direction and circumferential direction of said steel pipe and indicated or recorded.

7. A signal processing method, as in claim 2, wherein positions of piece cutting points corresponding to standard lengths of products are determined set in addition to the establishment of said inspection blocks.

8. A signal processing method according to claim 1, wherein an average inner diameter in each of said plurality of inspection blocks is calculated and discriminated in accordance with the measured outer diameter of said steel pipe in said positions of a piece cutting points and the wall thickness value data of each said plurality of inspection blocks and thereby the inner diameter at the pipe end is controlled by the average inner diameter.

9. A signal processing method, as in claim 4, wherein an average inner diameter in each of said plurality of inspection blocks is calculated in accordance with measured outer diameter of said steel pipe in said positions of a piece cutting points and the thickness value data and the wall thickness data of each said plurality of inspection blocks and thereby the inner diameter at the pipe end is controlled by the average inner diameter.

10. A signal processing method as in claim 2, wherein positions of piece cutting points are established in an intermediary portion of said steel pipe excluding the length of crop portions thereof.

11. A signal processing method according to claim 1, wherein the wall thickness value data of each of said plurality of inspection block is developed in the longitudinal direction and circumferential direction of said steel pipe and indicated or recorded.

* * * * *